United States Patent
Alon

(10) Patent No.: US 10,500,049 B2
(45) Date of Patent: Dec. 10, 2019

(54) FLEXIBLE RADIO-OPAQUE PROTRUSIONS FOR REVEALING THE POSITION OF A CONSTRICTING CORD OR ANNULUS RING PRIOR TO INSTALLATION ONTO A CARDIAC VALVE ANNULUS

(71) Applicant: Cardiac Implants LLC, Tarrytown, NY (US)

(72) Inventor: David Alon, Zichron Yaacov (IL)

(73) Assignee: Cardiac Implants LLC, Tarrytown, NY (US)

( * ) Notice: Subject to any disclaimer, the term of this patent is extended or adjusted under 35 U.S.C. 154(b) by 0 days.

(21) Appl. No.: 15/790,454

(22) Filed: Oct. 23, 2017

(65) Prior Publication Data

US 2018/0116800 A1    May 3, 2018

Related U.S. Application Data

(60) Provisional application No. 62/415,414, filed on Oct. 31, 2016.

(51) Int. Cl.
*A61F 2/24* (2006.01)
*A61B 17/068* (2006.01)
(Continued)

(52) U.S. Cl.
CPC .......... *A61F 2/2466* (2013.01); *A61B 17/068* (2013.01); *A61F 2/2445* (2013.01);
(Continued)

(58) Field of Classification Search
CPC .... A61F 2/2466; A61F 2/2445; A61F 2/2451; A61F 2220/0016; A61B 17/0469;
(Continued)

(56) References Cited

U.S. PATENT DOCUMENTS 9,517,130 B1    12/2016  Alon et al.
2006/0106305 A1*  5/2006  Lau .................. A61F 2/2451
                                                                600/431
(Continued)

FOREIGN PATENT DOCUMENTS

| JP | 2008536586 A | 9/2008 |
| WO | 2010091383 A2 | 8/2010 |
| WO | 2013088327 A1 | 6/2013 |

OTHER PUBLICATIONS

International Search Report and Written Opinion for application No. PCT/US2017/057811 dated Feb. 13, 2018.

*Primary Examiner* — Brian E Pellegrino
*Assistant Examiner* — Rebecca Lynee Zimmerman
(74) *Attorney, Agent, or Firm* — Potomac Law Group, PLLC

(57) ABSTRACT

A cord can be affixed to an annulus or adjacent tissue using anchors distributed about the cord to anchor respective regions of the cord to the annulus or adjacent tissue. Anchor launchers (which are supported by support arms) launch the anchors to embed them in the annulus or adjacent tissue. Flexible radio-opaque protrusions protrude distally beyond the anchor launchers. Progressive advancement of an anchor launcher in a distal direction beyond a point at which a protrusion makes contact with the annulus or adjacent tissue results in progressive deflection of the protrusion. This deflection can be visualized using fluoroscopy to ensure that the cord is positioned correctly before the anchors are launched. Some embodiments use an open loop of cord, in which case the cord can subsequently be used to constrict the annulus. Other embodiments use a closed loop of cord to prevent expansion of the annulus.

19 Claims, 8 Drawing Sheets

(51) Int. Cl.
   *A61B 17/115* (2006.01)
   *A61B 17/064* (2006.01)
   *A61B 17/00* (2006.01)
   *A61B 17/04* (2006.01)

(52) U.S. Cl.
   CPC ......... *A61F 2/2451* (2013.01); *A61B 17/1155* (2013.01); *A61B 2017/00243* (2013.01); *A61B 2017/00862* (2013.01); *A61B 2017/0409* (2013.01); *A61B 2017/0427* (2013.01); *A61B 2017/0437* (2013.01); *A61B 2017/0488* (2013.01); *A61B 2017/0647* (2013.01); *A61F 2220/0016* (2013.01); *A61F 2250/0098* (2013.01)

(58) Field of Classification Search
   CPC .......... A61B 17/068; A61B 2017/0409; A61B 2017/0427; A61B 2017/0488
   See application file for complete search history.

(56) References Cited

U.S. PATENT DOCUMENTS

| | | |
|---|---|---|
| 2011/0082538 A1 | 4/2011 | Dahlgren et al. |
| 2012/0296160 A1 | 11/2012 | Hill et al. |
| 2014/0309730 A1 | 10/2014 | Alon et al. |
| 2015/0257884 A1 | 9/2015 | Subramanian et al. |
| 2016/0120645 A1 | 5/2016 | Alon |

\* cited by examiner

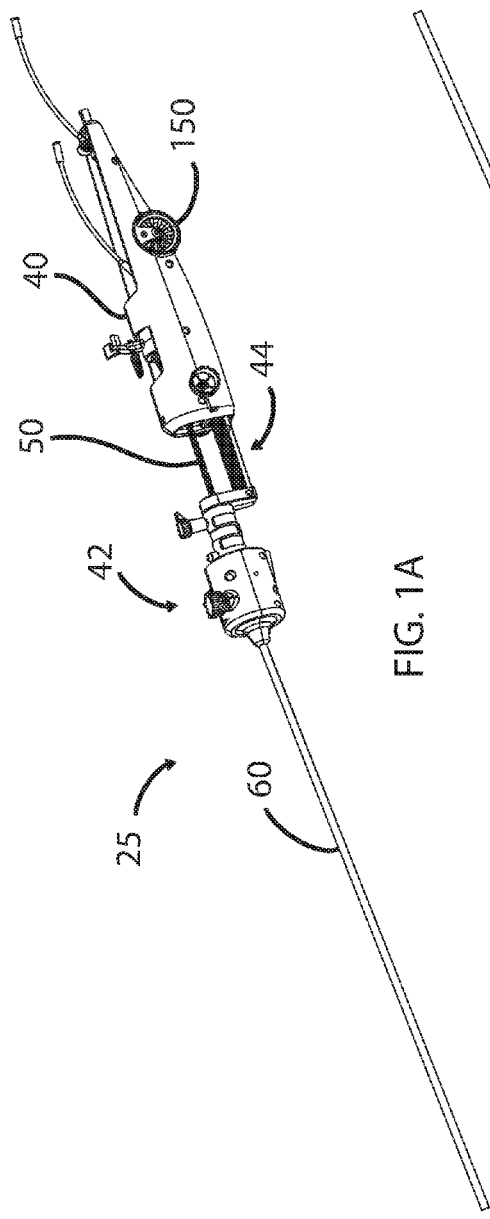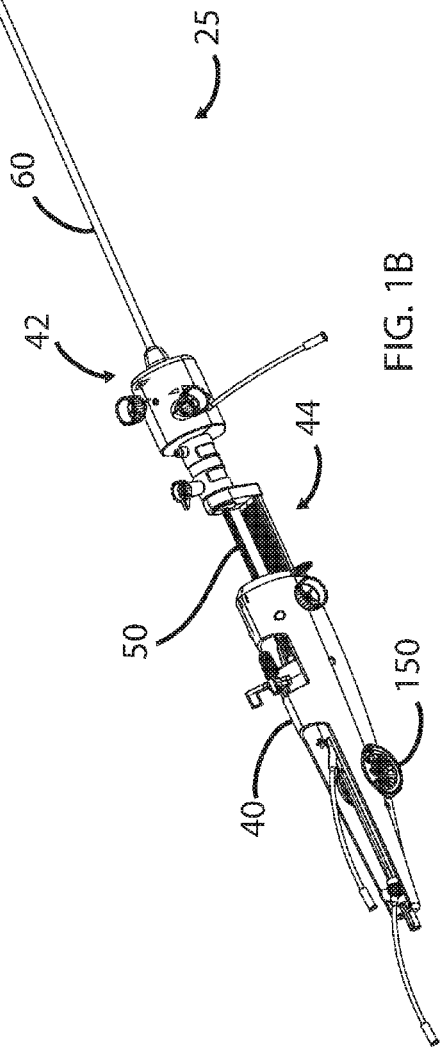
FIG. 1A
FIG. 1B

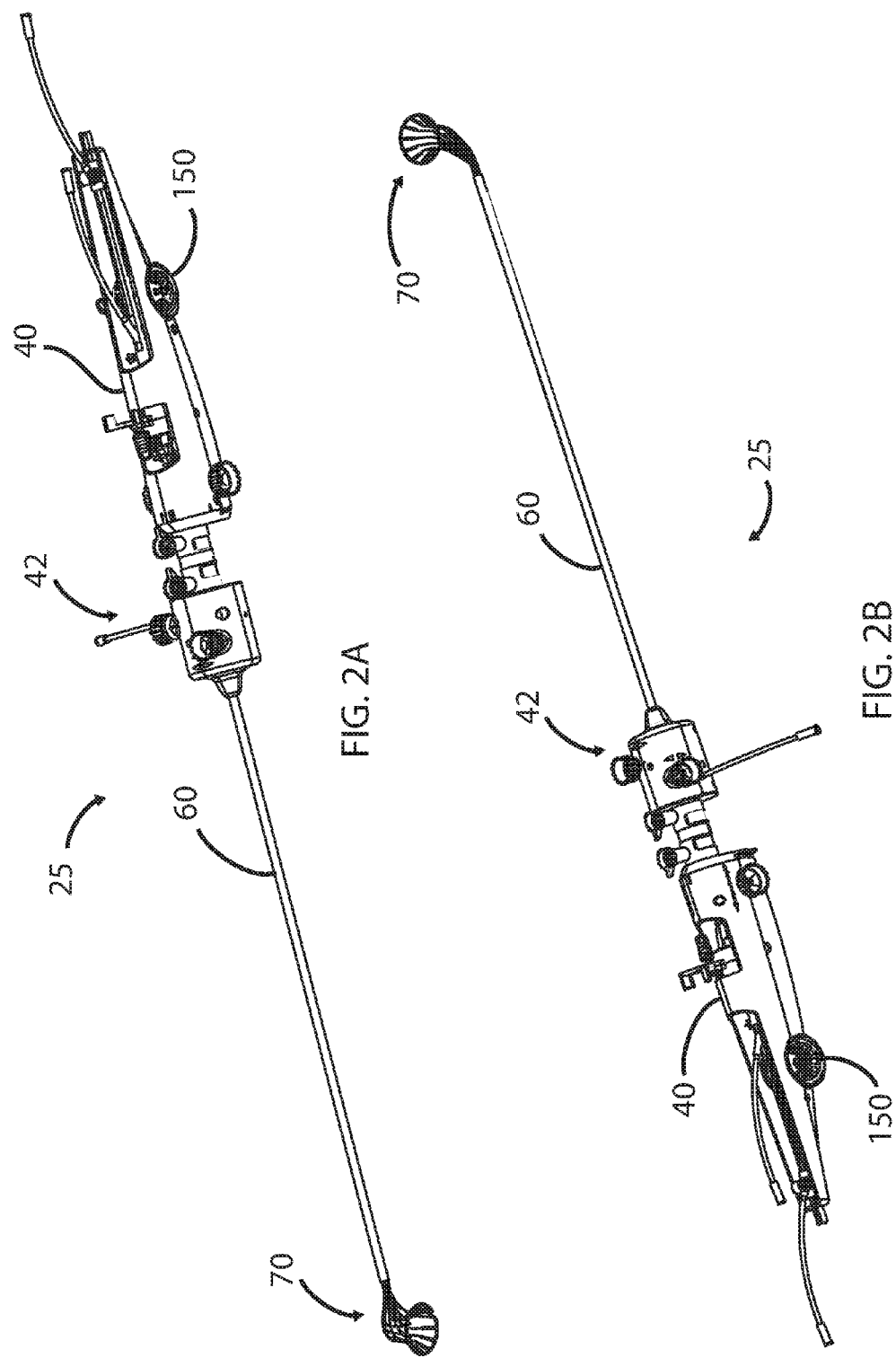

FLEXIBLE RADIO-OPAQUE PROTRUSIONS FOR REVEALING THE POSITION OF A CONSTRICTING CORD OR ANNULUS RING PRIOR TO INSTALLATION ONTO A CARDIAC VALVE ANNULUS

CROSS REFERENCE TO RELATED APPLICATIONS

This Application claims the benefit of U.S. Provisional Application 62/415,414, filed Oct. 31, 2016, which is incorporated herein by reference in its entirety.

BACKGROUND

A variety of approaches for delivering and installing a constricting cord (also referred to as a cinching cord) or an annulus ring to a cardiac valve annulus are described in U.S. application Ser. No. 14/364,060 (published as US 2014/0309730) and Ser. No. 14/895,711 (published as US 2016/0120645), each of which is incorporated by reference herein in its entirety.

SUMMARY OF THE INVENTION

One aspect of the invention is directed to a first apparatus for affixing a cord to an annulus. The first apparatus comprises a cord having a distal loop portion, and at least four anchors distributed about the cord. Each of the at least four anchors is configured to anchor a respective region of the cord to the annulus or to tissue adjacent to the annulus. The first apparatus also comprises at least four anchor launchers, at least four support arms, and at least four flexible radio-opaque protrusions. Each of the anchor launchers has a distal end, and each of the anchor launchers is configured to launch a respective one of the at least four anchors out of the anchor launcher's distal end so that the respective anchor becomes embedded in the annulus or the tissue adjacent to the annulus. Each of the support arms is shaped and arranged to support a respective one of the at least four anchor launchers so that the at least four support arms hold the distal ends of the anchor launchers at positions that correspond to a shape of the annulus, with the distal ends of the anchor launchers distributed about a perimeter of the shape of the annulus. Each of the protrusions is arranged with respect to a respective one of the at least four anchor launchers so that the protrusion is free to move from a relaxed state to a deflected state. In the relaxed state the protrusion protrudes distally beyond the distal end of the respective anchor launcher. Each of the protrusions is shaped and arranged so that progressive advancement of the respective anchor launcher in a distal direction beyond a point at which the protrusion makes contact with the annulus or the tissue adjacent to the annulus results in progressive deflection of the protrusion.

In some embodiments of the first apparatus, each of the protrusions extends between 4 and 10 mm from the distal end of the respective anchor launcher. In some embodiments of the first apparatus, each of the protrusions has a diameter between 0.05 and 0.3 mm.

In some embodiments of the first apparatus, in the relaxed state, each of the protrusions is bent at an angle between 5° and 20° with respect to a longitudinal axis of the respective anchor launcher. In some of these embodiments, in the relaxed state, each of the protrusions bends away from a centroid of the at least four anchor launchers.

In some embodiments of the first apparatus, each of the anchor launchers comprises a metal housing that is visualizable using fluoroscopy.

In some embodiments of the first apparatus, each of the protrusions is arranged so that when a protrusion in the deflected state is moved to a position at which the protrusion is no longer being pressed against the annulus or the tissue adjacent to the annulus, the protrusion returns towards the relaxed state.

In some embodiments of the first apparatus, each of the at least four anchor launchers comprises a housing shaped and dimensioned to accommodate a respective one of the at least four anchors, the housing having a distal end; a spring that is movable between a compressed state and an expanded state, arranged with respect to the housing and the respective anchor so that movement of the spring from the compressed state to the expanded state drives the respective anchor out of the distal end of the housing; and an actuator configured to trigger movement of the spring from the compressed state to the expanded state upon actuation of the actuator.

In some embodiments of the first apparatus, each of the protrusions is affixed to a respective anchor launcher by at least one weld. In some embodiments of the first apparatus, each of the protrusions is affixed to a respective pull wire that is used to trigger a respective anchor launcher.

In some embodiments of the first apparatus, the distal loop portion of the cord comprises an open loop having first and second ends, and the cord has first and second proximal portions connected, respectively, to the first and second ends of the distal loop portion. In other embodiments of the first apparatus, the distal loop portion of the cord is a closed loop.

Another aspect of the invention is directed to a first method for affixing a cord to an annulus. The first method comprises positioning, in a vicinity of the annulus, (a) a cord having a distal loop portion, (b) at least four anchors distributed about the cord, wherein each of the at least four anchors is configured to anchor a respective region of the cord to the annulus or to tissue adjacent to the annulus, (c) at least four anchor launchers, each of the anchor launchers having a distal end, wherein each of the anchor launchers is configured to launch a respective one of the at least four anchors out of the anchor launcher's distal end so that the respective anchor becomes embedded in the annulus or the tissue adjacent to the annulus, and (d) at least four flexible radio-opaque protrusions, wherein each of the protrusions is arranged with respect to a respective one of the at least four anchor launchers so that the protrusion is free to move from a relaxed state to a deflected state. In the relaxed state each of the protrusions protrudes distally beyond the distal end of the respective anchor launcher. Each of the protrusions is shaped and arranged so that progressive advancement of the respective anchor launcher in a distal direction beyond a point at which the protrusion makes contact with the annulus or the tissue adjacent to the annulus results in progressive deflection of the protrusion. The first method also comprises adjusting a position of the anchor launchers until fluoroscopic images of the protrusions indicate that each of the protrusions is deflected beyond a threshold angle; and triggering each of the anchor launchers to launch a respective anchor at a time when fluoroscopic images of the protrusions indicate that each of the protrusions is deflected beyond the threshold angle.

In some embodiments of the first method, each of the protrusions extends between 4 and 10 mm from the distal end of the respective anchor launcher. In some embodiments of the first method, each of the protrusions has a diameter between 0.05 and 0.3 mm.

In some embodiments of the first method, each of the protrusions is arranged so that when a protrusion in the deflected state is moved to a position at which the protrusion is no longer being pressed against the annulus or the tissue adjacent to the annulus, the protrusion returns towards the relaxed state.

Another aspect of the invention is directed to a second method for aligning a device with a target location. The second method comprises arranging at least three flexible radio-opaque protrusions with respect to the device so that each of the protrusions is free to move from a relaxed state to a deflected state, wherein in the relaxed state the protrusion protrudes distally beyond the device, and wherein each of the protrusions is shaped and arranged so that progressive advancement of the device in a distal direction beyond a point at which the protrusion makes contact with a structure in the target location results in progressive deflection of the protrusion, and wherein each of the protrusions is arranged so that when a protrusion in the deflected state is moved to a position at which the protrusion is no longer being pressed against the structure, the protrusion returns towards the relaxed state. The second method also comprises positioning the device in a vicinity of the target location; adjusting a position of the device until fluoroscopic images of the protrusions indicate that each of the protrusions is deflected beyond a threshold angle; and releasing the device at a time when fluoroscopic images of the protrusions indicate that each of the protrusions is deflected beyond the threshold angle.

Some embodiments of the second method further comprise anchoring the device in place at the time when fluoroscopic images of the protrusions indicate that each of the protrusions is deflected beyond the threshold angle.

In some embodiments of the second method, each of the protrusions extends distally beyond the device by between 4 and 10 mm. In some embodiments of the second method, each of the protrusions has a diameter between 0.05 and 0.3 mm.

BRIEF DESCRIPTION OF THE DRAWINGS

FIGS. 1A and 1B are left and right side views, respectively, of an embodiment of an apparatus for installing a constricting cord or an annulus ring onto a cardiac valve annulus when the outer sleeve is in an extended position.

FIGS. 2A and 2B are left and right side views, respectively, of the FIG. 1 embodiment as it appears when the outer sleeve is in a retracted position.

DESCRIPTION OF THE PREFERRED EMBODIMENTS

Figure 3A:
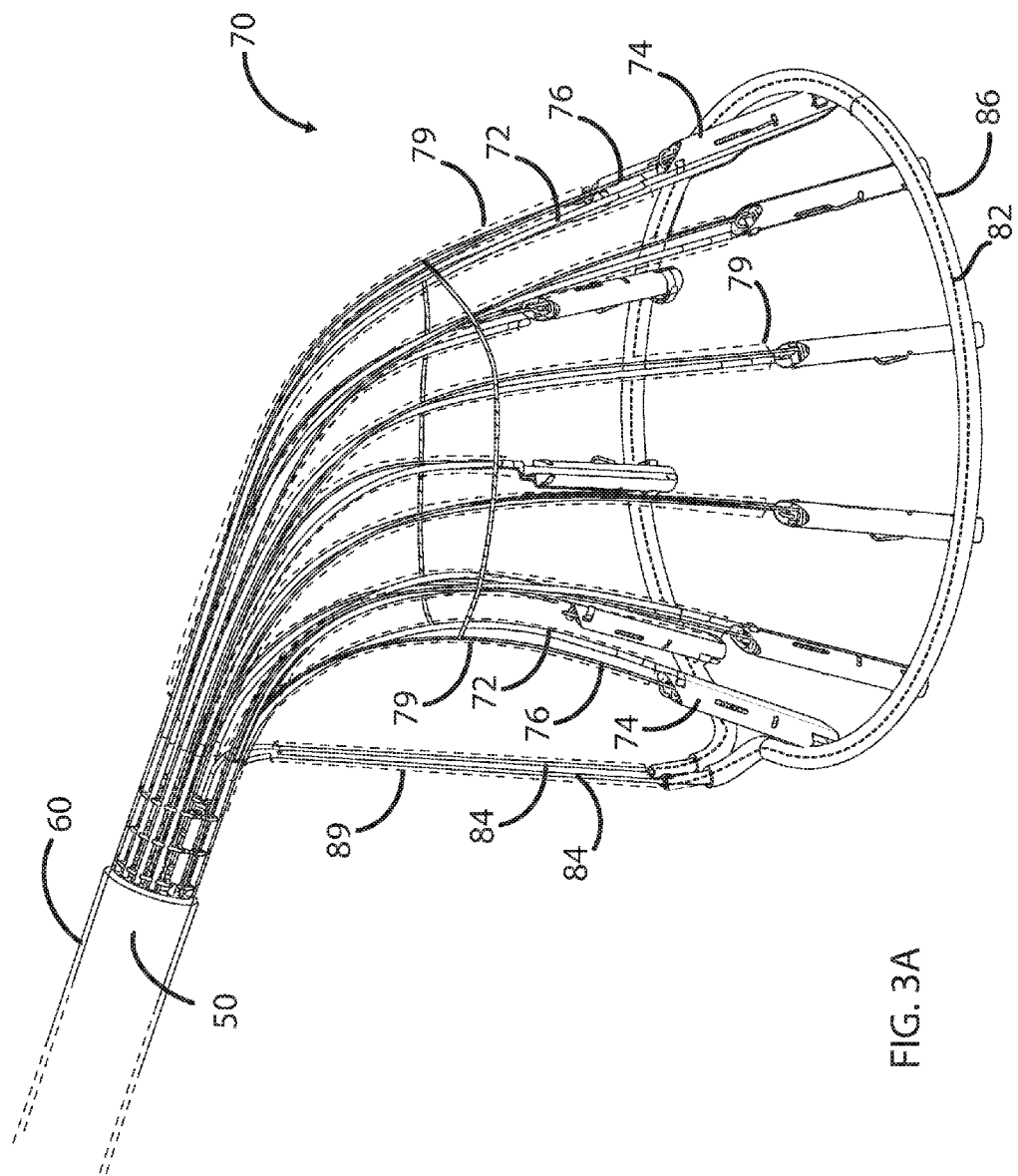
FIG. 3A is a detailed view of a distal assembly that has emerged from within the outer sleeve in the FIG. 2 embodiment.

This application describes methods and apparatuses for delivering and installing a constricting cord or an annulus ring into a cardiac valve annulus. In the constricting cord embodiments, a cord with an open distal loop is installed into a cardiac valve annulus using the apparatuses and/or methods described herein, and after waiting for tissue ingrowth to occur, the cord can be constricted in order to reduce the diameter of the annulus. These embodiments are useful for correcting or improving a variety of valve-related conditions (including but not limited to mitral valve regurgitation). In the annulus ring embodiments, an annulus ring (i.e., a closed loop of cord) is installed into a cardiac valve annulus to either (a) stabilize the shape of the annulus and prevent the annulus from expanding or (b) serve as the foundation onto which a replacement valve can be mounted. These embodiments are useful in the contexts of reducing valve regurgitation and cardiac valve replacement.

FIGS. 1A, 1B, 2A, and 2B are views of an apparatus 25 for delivering and installing a cord onto a cardiac valve annulus, such as the mitral valve annulus or the tricuspid valve annulus. In all four of these figures, the housing 40 is disposed on the proximal side of the apparatus 25, and an outer sleeve 60 is disposed at the distal side of the apparatus. More specifically, FIGS. 1A and 1B are left and right side views, respectively, of the apparatus 25 as it appears when the outer sleeve 60 of the apparatus is in an extended position; and FIGS. 2A and 2B are left and right side views, respectively, of the same apparatus 25 as it appears when the outer sleeve 60 is in a retracted position. When the outer sleeve 60 is retracted (as shown in FIGS. 2A and 2B), the distal assembly 70 (which includes the distal loop portion of the cord) extends out past the distal end of the outer sleeve 60. When the outer sleeve 60 is extended (as shown in FIGS. 1A and 1B), the distal assembly is collapsed and is disposed within the outer sleeve 60, and is therefore not visible in those figures. The extension and retraction of the outer sleeve 60 with respect to the core 50 is controlled by the sleeve retractor 44.

FIG. 3A is a detailed view of a distal assembly 70 that has emerged from within the outer sleeve 60 as a result of the retraction of the outer sleeve 60, so that the distal assembly 70 extends distally beyond the distal end of the outer sleeve 60. The distal assembly 70 in the illustrated embodiment includes ten anchor launchers 74, each of which is supported by its own individual support arm 72. But in alternative embodiments, a different number of support arms 72 and anchor launchers 74 may be used (e.g., between 4 and 16 support arms and between 4 and 16 anchor launchers).

The at least four support arms 72 are mounted to the core 50. The support arms 72 extend distally beyond the distal end of the core. Suitable materials for forming the support arms 72 include stainless steel, nitinol, and other biocompatible metals. The support arms are flexible enough to collapse within the outer sleeve 60 (as seen in FIG. 1), but spring back to their original shape when extended distally beyond the confines of the outer sleeve 60 (as seen in FIGS. 2 and 3A).

At least four anchor launchers 74 are supported by respective ones of the at least four support arms 72. Each of the anchor launchers has a distal end. Suitable designs for the anchor launchers and the anchors contained therein can be found in U.S. application Ser. No. 14/895,711 (US2016/0120645) and U.S. Pat. No. 9,517,130, each of which is incorporated herein by reference. An anchor is disposed in each of the anchor launchers 74. Each of the anchor launchers 74 is has a pull-wire trigger, and each of the pull wires 76 is operatively connected to one of the anchor launchers 74 so that pulling on a respective pull wire will launch the respective anchor out of the distal end of the anchor launcher 74 so that the respective anchor becomes embedded in the annulus or the tissue adjacent to the annulus.

When the outer sleeve 60 is in the extended position (as it is in FIG. 1), the support arms 72 and the anchor launchers 74 are all disposed within the outer sleeve 60, and the support arms 72 are collapsed to fit inside the outer sleeve 60. But when the outer sleeve 60 is in the retracted position (as it is in FIGS. 2 and 3A), the anchor launchers 74 and at least a portion of the support arms 72 extend distally beyond the distal end of the outer sleeve 60. The support arms are shaped such that when the outer sleeve 60 is in the retracted position, the support arms 72 hold the distal ends of the anchor launchers 74 at positions that correspond to a shape of the annulus, with the distal ends of the anchor launchers 74 distributed about a perimeter of the shape of the annulus.

A constricting cord has a distal loop portion 82, a first proximal portion 84, and a second proximal portion 84. The distal loop portion 82 of the cord is preferably surrounded by a sleeve 86 of material that promotes tissue ingrowth. The sleeve 86 is preferably soft and flexible. Suitable materials include fabric braids (e.g., made of polyethylene terephthalate (PET) fabric. Preferably, all three portions of the constricting cord (i.e., the distal loop portion 82, the first proximal portion 84, and the second proximal portion 84 are all regions of a single continuous cord). Examples of suitable materials for the constricting cord include ultra-high-molecular-weight polyethylene (e.g., Dyneema®) and other strong and flexible materials.

Figure 3B:
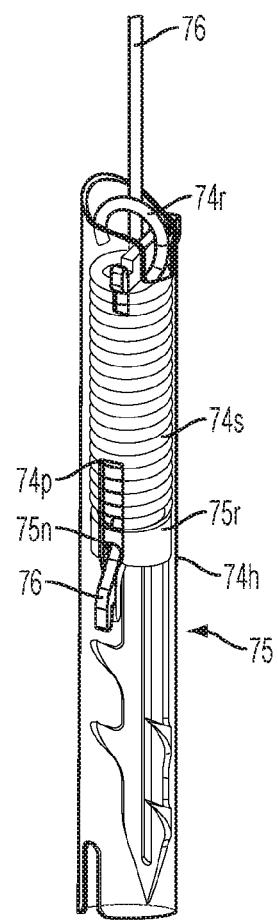
FIG. 3B is a detailed view of the pre-launched state of the anchor launchers of the FIG. 3A embodiment.
Figure 3C:
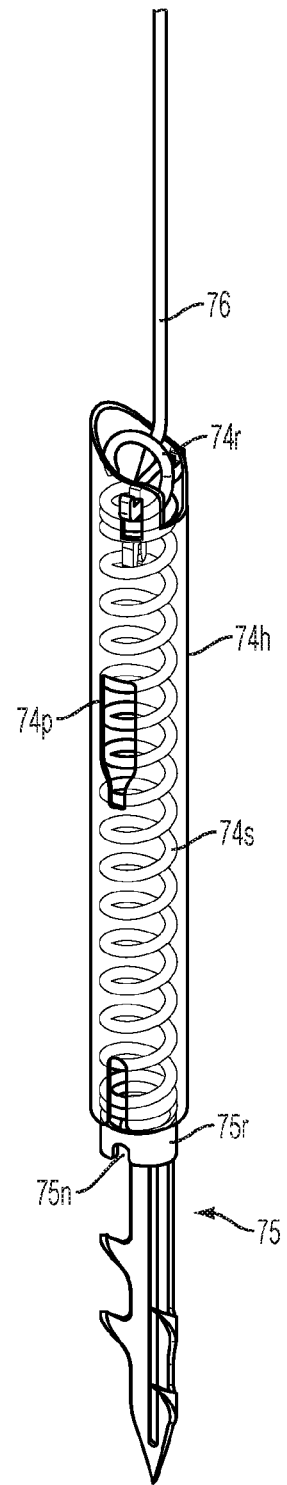
FIG. 3C is a detailed view of the post-launching state of the anchor launchers of the FIG. 3A embodiment.

Each of the anchor launchers 74 houses and anchor (75, shown in FIGS. 3B and 3C). These anchors are distributed about the distal loop portion 82 of the cord and connected to the distal loop portion 82 of the cord, and each of the anchors is configured to anchor a respective region of the distal loop portion 82 of the cord to the annulus or to tissue adjacent to the annulus. In some embodiments, the connection between the anchors 75 and the distal loop portion 82 of the cord is implemented by running the distal loop portion 82 of the cord through a slot in each of the anchors. In alternative embodiments, this connection is implemented by connecting the anchors to the sleeve 86 that surrounds the distal loop portion 82 of the cord, or to one or more different intervening members (not shown) that link each of the anchor 75 to the distal portion 82 of the cord.

Note that the shape of the distal loop portion 82 of the cord in FIG. 3A is round, and this shape is suitable when the cord is installed onto a round annulus. In alternative embodiments, when the cord is installed onto an annulus with a different shape (e.g., a mitral valve annulus that is D-shaped), the support arms 72 are pre-shaped so that the distal ends of the anchor launchers 74 will be distributed about the perimeter of that differently-shaped annulus prior to implantation. This will result in a D-shaped distal loop portion 82 subsequent to implantation.

Preferably, the shape and size of the support arms 72 are designed to fit the anatomy of the individual patient, so that when the outer sleeve 60 is retracted, the distal loop portion 82 of the cord will be opened by the support arms 72 and spread around the annulus, so that it will be in the correct location ready for the anchors to be launched with little adjustment. This may be achieved by designing the 3D shape of the support arms 72 so that they each extend in a predefined angulation from the core 50. When a cord is being installed on the tricuspid valve annulus, the support arms 72 are preferably shaped so that none of the anchor launchers 74 will be positioned on or adjacent to the AV node to prevent potential damage to that node.

FIG. 3A also depicts a set of sleeves 79, 89. As explained above, each of the anchor launchers 74 is supported by one of the support arms 72 and is actuated by one of the pull wires 76. To facilitate smoother opening of the support arms 72 into the configuration depicted in FIG. 3A, it is preferable to surround the support arm 72 and the pull wire 76 that terminate at each individual anchor launcher 74 in a sleeve 79. In this embodiment, there will be one sleeve 79 for each of the anchor launchers 74, and the support arms 72 and the pull wires 76 for that anchor launcher 74 will run through the center of the corresponding sleeve 79. In some embodiments, these sleeves 79 are made from clear shrink tubing with an inner diameter (after shrinking) that is large enough so as not to interfere with the slidability of the pull wires 76 within the sleeves 79. In alternative embodiments, the sleeves 79 may be made from other polymer materials with a similar inner diameter.

Optionally, an additional sleeve 89 is provided, and the proximal portions 84 of the cord run through this additional sleeve 89. The sleeve 89 is similar to the sleeve 79 discussed above, and is dimensioned to have an inner diameter that is large enough so as not to interfere with the slidability of the proximal portions 84 of the cord within the sleeve 89.

The distal ends of the anchor launchers 74 are pressed against the annulus and, after proper positioning has been confirmed (e.g. using fluoroscopy and echo imaging), the anchor launchers 74 are triggered by pulling on the proximal ends of the pull wires 76. This causes each of the anchor launchers 74 to launch its anchor into the annulus. Preferably, all of the anchors launchers 74 are triggered simultaneously.

FIGS. 3B and 3C illustrate an example of one way to implement the anchor launchers 74. Each anchor launcher 74 includes a housing 74h that has an open front end. The housing 74h has a cylindrical interior void. An anchor 75 is disposed in the front section of the void in the housing, and an anchor launching spring 74s is disposed in the rear portion of the void in the housing 74h in a compressed state. The spring 74s is preferably a coil spring. In the illustrated embodiment, the back end (i.e., the proximal end) of the spring 74s is retained in housing 74h by a spring retention loop or hook 74r.

Each anchor launcher 74 includes an actuator configured to prevent the spring from expanding from the compressed state prior to being actuated, and to permit the spring to expand from the compressed state upon being actuated. In the illustrated embodiment, the actuator is implemented using a pull wire 76 that initially passes coaxially through the anchor launching spring 74s.

In the initial state (i.e., prior to actuation) depicted in FIG. 3B, the distal portion of the pull wire 76 passes through and interfaces with an opening 74p in the sidewall of the housing 74*h*. The front end (i.e., the distal end) of the spring 74*s* presses against the back end of the anchor 75. In the illustrated embodiment, the back end of the anchor is a ring-shaped section 75*r*. Prior to actuation, the pull wire 76 passes through the notch 75*n* in the ring 75*r* at the back of the anchor 75 and also passes through the opening 74*p* of the housing 74*h*. The presence of the distal portion of the pull wire 76 in this position, engaged with the opening 74*p*, prevents the spring 74*s* from expanding, thereby keeping the spring 74*s* in a compressed state.

When the pull wire 76 is pulled in a proximal direction, the distal portion of pull wire 76 is pulled inwardly through the opening 74*p* and is withdrawn from the opening 74*p*. At this point, the spring 74*s* will expand into the front section of the housing 74*h* and push the anchor 75 forward such that the anchor 75 exits the front end of housing, as depicted in FIG. 3C. The spring 74*s* pushes the anchor 75 with sufficient force to implant the anchor into the annulus or into tissue adjacent to the annulus. It is preferable to pull the wire 76 in the proximal direction with a jerk (i.e., with rapid acceleration), because it makes the launching more reliable and prevents the anchor launcher 74 from lifting away from the surface of the target tissue prior to implantation.

Figure 4B:
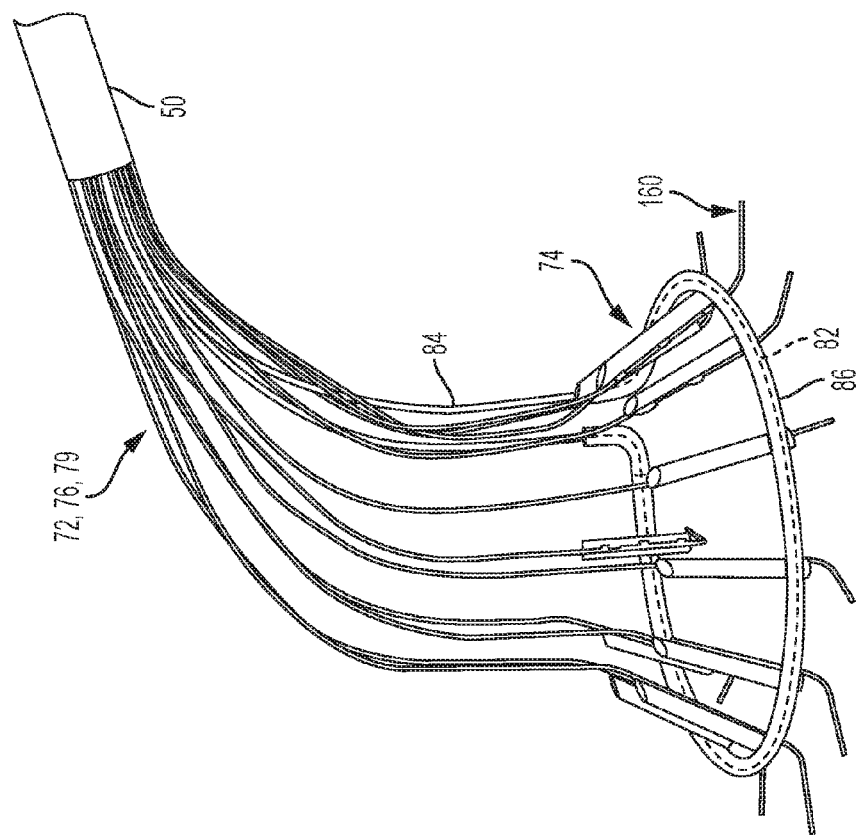
FIG. 4B depicts the FIG. 4A embodiment with the position-revealing protrusions disposed in a deflected state.
Figure 4A:
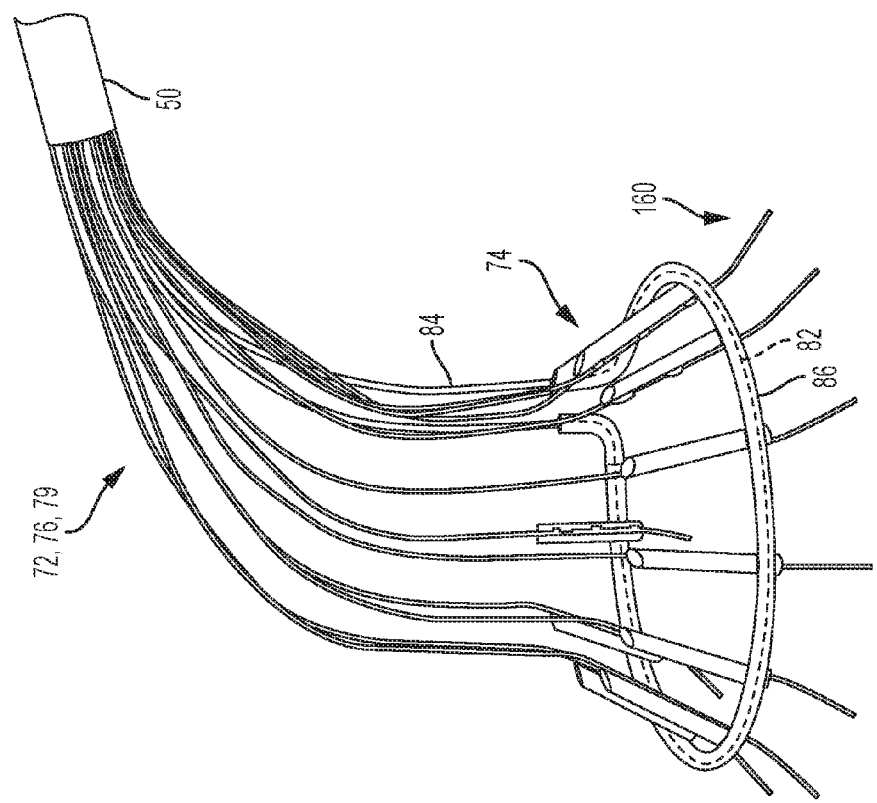
FIG. 4A depicts a first embodiment for confirming the position of the anchor launchers with position-revealing protrusions disposed in a relaxed state.

FIG. 4A depicts a first embodiment for confirming that the distal ends of the anchor launchers 74 are pressed against the annulus before the anchor launchers 74 are triggered. This embodiment operates in the same way as the FIG. 3A-C embodiment described above and includes the various components described in connection with those figures, except that the FIG. 4A embodiment includes one additional set of elements—the flexible radio-opaque protrusions 160. Note that the same reference numbers are used in FIG. 3A-C and FIGS. 4A-4D to denote corresponding elements.

In this FIG. 4A embodiment, the flexible radio-opaque protrusions 160 are attached to the anchor launchers 74 so that in their initial relaxed state, the protrusions 160 protrude distally beyond the distal end of the anchor launchers 74. In some embodiments, the protrusions 160 extend between 4 and 10 mm beyond the distal end of the anchor launchers 74. In some embodiments, the diameter of the protrusions 160 is between 0.05 and 0.3 mm. In some embodiments, the protrusions 160 are preferably bent radially outward at a small angle (e.g., 5-20°) with respect to an axis defined by each anchor launcher 74. In alternative embodiments (not shown) the protrusions 160 are parallel to the axis defined by each anchor launcher 74.

Each of the protrusions 160 is arranged with respect to a respective anchor launcher 74 so that the protrusion 160 is free to move from a relaxed state to a deflected state. The protrusions 160 preferably have sufficient flexibility such that progressive advancement of the respective anchor launcher in a distal direction beyond a point at which the protrusion makes contact with the annulus or the tissue adjacent to the annulus results in progressive deflection (or bending) of the protrusion as the distal end of the anchor launcher 74 is pushed towards the annulus. In the FIG. 4A/B embodiment, each of the protrusions 160 will be progressively deflected or bent further outward until it reaches the flattened configuration depicted in FIG. 4B. In the flattened configuration, the protrusions 160 will be deflected or bent radially outward at a much larger angle (e.g., 70-90°) as depicted in FIG. 4B. In alternative embodiments (not shown), the protrusions will deflect or bend radially inward instead of outward at a similar larger angle. Note that as the flexible radio-opaque protrusions 160 are progressively moved closer and closer to the annulus, the angle of deflection or bending of the protrusions 160 with respect to the axis defined by each anchor launcher 74 will progressively increase until it reaches the maximum angle.

The angles of each of the protrusions 160 with respect to an axis defined by each anchor launcher 74 can be visualized from outside the subject body using fluoroscopy to determine if the distal end of each of the anchor launchers 74 has made contact with the annulus. Note that the anchor launchers 74 themselves are preferably made of metal such as stainless steel that can be visualized using fluoroscopy. If it appears that any of the protrusions 160 has not been fully deflected or bent into its flattened configuration (which indicates that the distal end of the anchor launcher 74 is not sufficiently close to the annulus or to tissue adjacent to the annulus), the entire distal assembly 70 can be repositioned by manipulating the controls back at the proximal end of the device until all of the protrusions 160 have been moved into their flattened configuration. After all of the protrusions 160 are positioned in their flattened configuration (which indicates that the distal end of each of the anchor launchers 74 is contacting the annulus), the anchor launchers 74 are triggered.

Suitable materials for making the radio-opaque protrusions 160 include wires made from radio-opaque alloys (e.g. 80% platinum and 20% iridium, gold alloys, and platinum alloys), or other alternatives that will be apparent to persons skilled in the relevant arts. The protrusions 160 should be flexible enough to deflect or bend when they are pressed against the annulus by manipulation of the catheter body or the controls disposed on the proximal side of the apparatus 25 (shown in FIGS. 1-2). Whenever a protrusion 160 that has been pressed against the annulus is pulled back into a position at which it no longer presses against the annulus or the tissue adjacent to the annulus, the protrusion 160 preferably springs back towards it original relaxed state.

Figure 4D:
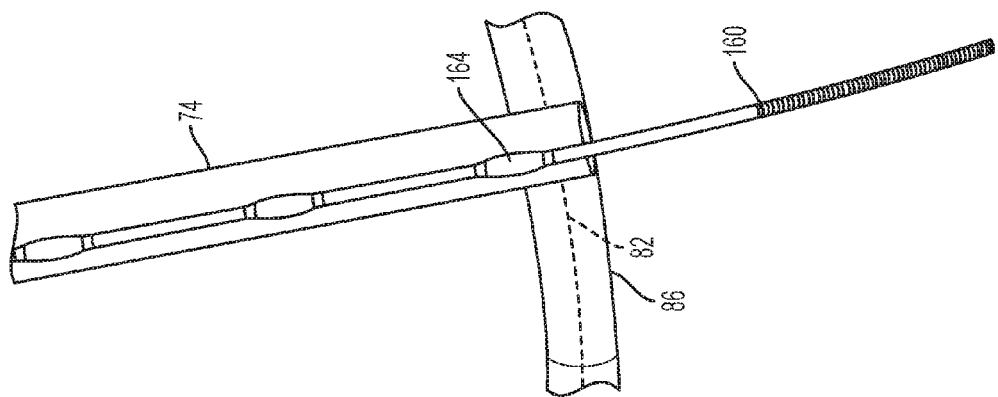
FIG. 4D depicts a detail of FIG. 4C.
Figure 4C:
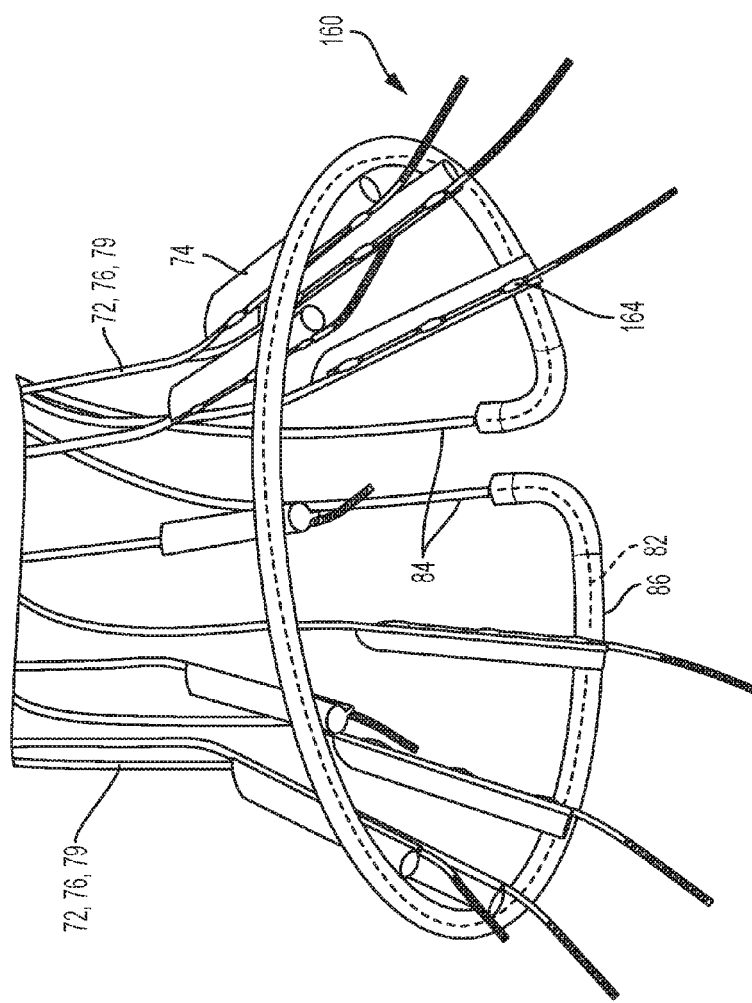
FIG. 4C depicts a detail of the FIG. 4A embodiment.

FIG. 4C depicts a detail of the FIG. 4A embodiment when the flexible radio-opaque protrusions 160 are disposed in their original small-angle configuration (i.e., the original relaxed state). FIG. 4D depicts one approach for affixing the protrusions 160 to the anchor launchers 74 using a plurality of welding points 164. A wide variety of alternative approaches for attaching the protrusions 160 to the anchor launchers 74 can be readily envisioned, including but not limited to adhesives and fasteners.

Figure 5A:
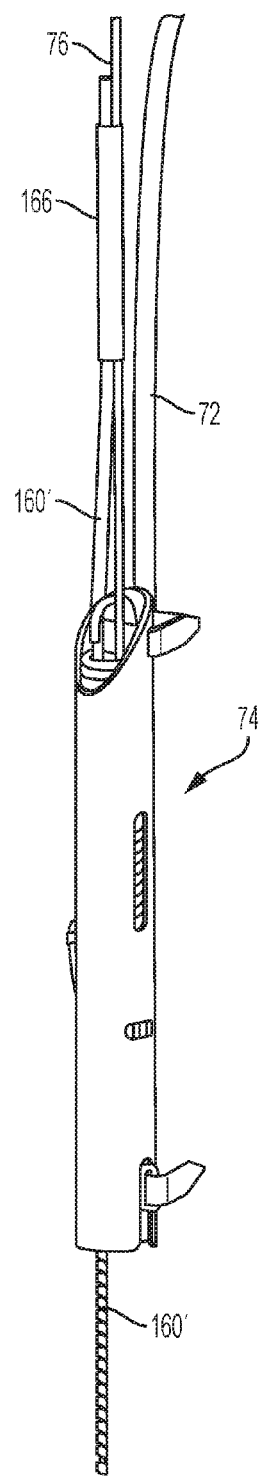
FIG. 5A depicts an alternative embodiment for implementing position-revealing protrusions that protrude from the anchor launchers, with the position-revealing protrusions in a relaxed state.
Figure 5B:
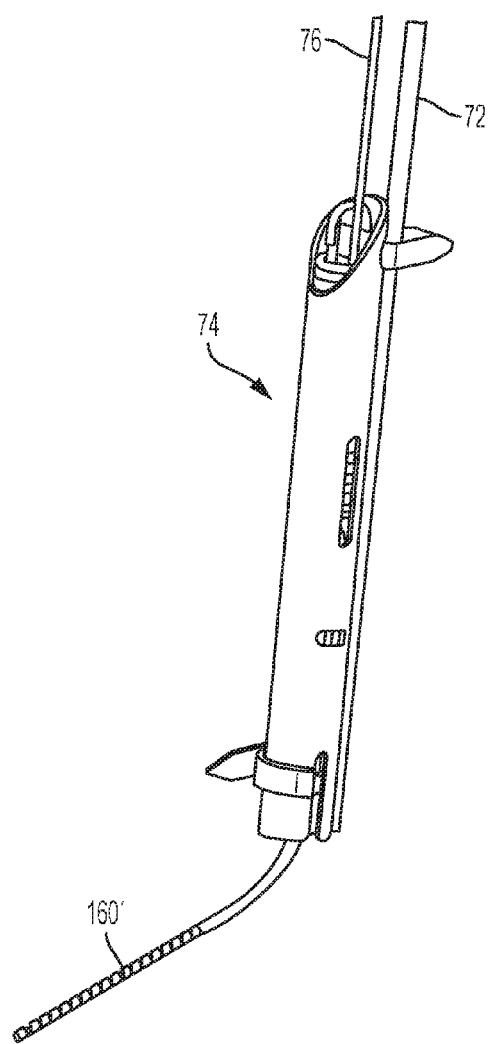
FIG. 5B depicts the FIG. 5A embodiment with the position-revealing protrusions disposed in a deflected state.

FIGS. 5A-5D depicts an alternative embodiment for implementing flexible radio-opaque protrusions 160' that protrude from anchor launchers 74. These flexible radio-opaque protrusions 160' are similar to the corresponding protrusions 160 in the FIG. 4 embodiment, except that in the FIG. 5 embodiment, instead of welding the protrusions 160' to the anchor launchers 74, the protrusions 160' are connected to the pull wires 76 that are used for triggering the anchor launcher 74. One suitable approach for making the connection between the protrusions 160' and the pull wires 76 is to crimp those two components together using a crimped tube 166. Alternative approaches for making that connection include adhesives, knots, etc. and will be apparent to persons skilled in the relevant arts. FIG. 5A depicts this embodiment with the protrusions 160' in the relaxed/extended state, and FIG. 5B depicts this embodiment with the protrusions 160' in the deflected/flattened state.

Figure 5C:
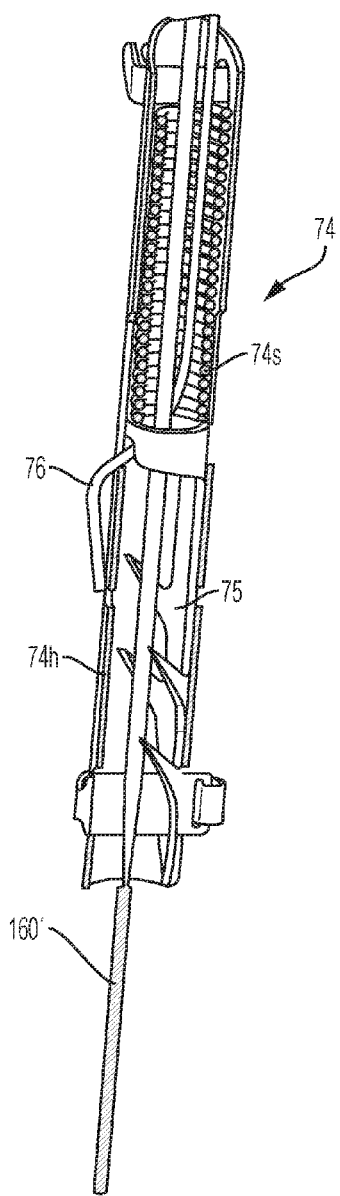
FIG. 5C is a cut-away detail of the FIG. 5A embodiment when the anchor has not yet been launched out of the anchor launcher.
Figure 5D:
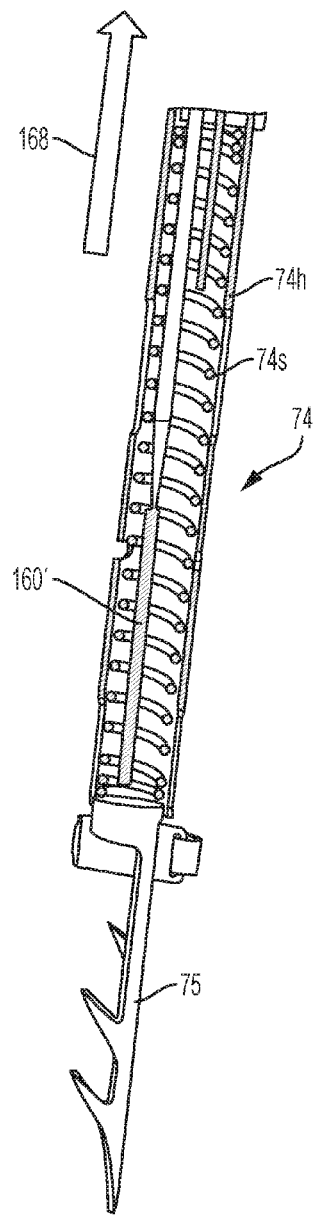
FIG. 5D is a detail of the FIG. 5A embodiment after the anchor has been launched.

FIG. 5C is a cut-away detail of the FIG. 5A embodiment showing that when the anchor 75 has not yet been launched out of the anchor launchers 74, the flexible radio-opaque protrusions 160' pass through the center of the anchor 75 before passing distally beyond the distal end of the anchor launcher 74. And FIG. 5D is a detail of the FIG. 5A embodiment showing that after the anchor 75 has been launched out of the anchor launchers 74, both the pull wire 76 and the protrusions 160' are withdrawn in a proximal direction 168.

Any of the embodiments described above in connection with FIGS. 4-5 may be used to implement a method for affixing a cord to an annulus. This method includes positioning, in a vicinity of the annulus, (a) a cord 82 having a distal loop portion, (b) at least four anchors 75 distributed about the cord, wherein each of the at least four anchors 75 is configured to anchor a respective region of the cord 82 to the annulus or to tissue adjacent to the annulus, (c) at least four anchor launchers 74, each of the anchor launchers having a distal end, wherein each of the anchor launchers 74 is configured to launch a respective one of the at least four anchors 75 out of the anchor launcher's distal end so that the respective anchor becomes embedded in the annulus or the tissue adjacent to the annulus, and (d) at least four flexible radio-opaque protrusions 160, each of the protrusions is arranged with respect to a respective one of the at least four anchor launchers 74 so that the protrusion 160 is free to move from a relaxed state to a deflected state, wherein in the relaxed state the protrusion protrudes distally beyond the distal end of the respective anchor launcher 74, and wherein each of the protrusions 160 is shaped and arranged so that progressive advancement of the respective anchor launcher 74 in a distal direction beyond a point at which the protrusion 160 makes contact with the annulus or the tissue adjacent to the annulus results in progressive deflection of the protrusion 160.

This method also includes adjusting a position of the anchor launchers 74 until fluoroscopic images of the protrusions 160 indicate that each of the protrusions is deflected beyond a threshold angle; and triggering each of the anchor launchers 74 to launch a respective anchor 75 at a time when fluoroscopic images of the protrusions 160 indicate that each of the protrusions is deflected beyond the threshold angle. The value of the threshold angle that indicates that the distal end of each anchor launcher 74 is sufficiently close to the annulus (or the tissue adjacent to the annulus) will depend on the geometry of the protrusion 160 with respect to the anchor launcher 74. In some embodiments, the threshold angle will correspond to at least 15° of additional deflection above and beyond the bending angle that corresponds to the initial relaxed state (e.g., above and beyond the initial angle of 5-20° for the FIG. 4A embodiment).

Preferably, each of the protrusions 160 that is used in connection with implementing this method is arranged so that when a protrusion 160 in the deflected state is moved to a position at which the protrusion is no longer being pressed against the annulus or the tissue adjacent to the annulus, the protrusion returns towards the relaxed state.

The embodiments described above in connection with FIGS. 4-5 rely on tissue ingrowth to strengthen the bond between the distal loop portion 82 of the cord and the annulus. In these embodiments, the distal loop portion 82 of the cord is attached to the annulus by anchoring the sleeve 86 (through which the distal loop portion 82 runs) to the annulus using the anchors 75. Immediately after implantation, the bond between the distal loop portion 82 the annulus is typically not strong enough to withstand constricting. But because the sleeve 86 is made of material that accepts tissue ingrowth, ingrowth of tissue at the annulus into the sleeve 86 will begin to occur after implantation. This tissue ingrowth will eventually (e.g. over the course of 2-12 weeks) strengthen the bond between the sleeve 86 and the annulus until the bond is strong enough to withstand constricting.

In alternative embodiments, the constricting cord 82 with an open distal loop shown in FIGS. 4A-4C is replaced with an annulus ring (not shown), which is a closed loop of cord. In these embodiments, instead of implanting the distal loop portion 82 of a cord into the annulus so that the proximal portions 84 of the cord extend backwards into the core 50 (as described above), a closed loop of cord is implanted into the annulus or into tissue adjacent to the annulus. Preferably, the closed loop of cord is surrounded by a sleeve in a manner similar to the way that the distal loop portion 82 of the cord was enclosed in a sleeve 86 in the FIGS. 4A-4C embodiment.

The concepts described herein are not limited to the context of installing rings or constricting cords to cardiac valve annuli, and may be extended to other situations including but not limited to an annulus in a subject's gastrointestinal tract. For example, a device may be aligned with a target location using the following method.

First, at least three flexible radio-opaque protrusions are arranged with respect to the device so that each of the protrusions is free to move from a relaxed state to a deflected state, wherein in the relaxed state the protrusion protrudes distally beyond the device. Each of the protrusions is shaped and arranged so that progressive advancement of the device in a distal direction beyond a point at which the protrusion makes contact with a structure in the target location results in progressive deflection of the protrusion. And each of the protrusions is arranged so that when a protrusion in the deflected state is moved to a position at which the protrusion is no longer being pressed against the structure, the protrusion returns towards the relaxed state.

The device is then positioned in a vicinity of the target location. The position of the device is then adjusted until fluoroscopic images of the protrusions indicate that each of the protrusions is deflected beyond a threshold angle. Finally, the device is released at a time when fluoroscopic images of the protrusions indicate that each of the protrusions is deflected beyond the threshold angle. Depending on the nature of the device, the device may be anchored in place at the time when fluoroscopic images of the protrusions indicate that each of the protrusions is deflected beyond the threshold angle.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for affixing a cord to an annulus, the apparatus comprising:
    a cord having a distal loop portion;
    at least four anchors distributed about the cord, wherein each of the at least four anchors is configured to anchor a respective region of the cord to the annulus or to tissue adjacent to the annulus;
    at least four anchor launchers, each of the anchor launchers having a distal end, wherein each of the anchor launchers is configured to launch a respective one of the at least four anchors out of the anchor launcher's distal end so that the respective anchor becomes embedded in the annulus or the tissue adjacent to the annulus;

at least four support arms, each of the support arms is shaped and arranged to support a respective one of the at least four anchor launchers so that the at least four support arms hold the distal ends of the anchor launchers at positions that correspond to a shape of the annulus, with the distal ends of the anchor launchers distributed about a perimeter of the shape of the annulus; and at least four flexible radio-opaque protrusions, each of the protrusions is arranged with respect to a respective one of the at least four anchor launchers so that the protrusion is free to move from a relaxed state to a deflected state, wherein in the relaxed state the protrusion protrudes distally beyond the distal end of the respective anchor launcher, and wherein each of the protrusions is shaped and arranged so that progressive advancement of the respective anchor launcher in a distal direction beyond a point at which the protrusion makes contact with the annulus or the tissue adjacent to the annulus results in progressive deflection of the protrusion, and wherein in the relaxed state, each of the protrusions is bent at an angle between 5° and 20° with respect to a longitudinal axis of the respective anchor launcher.

2. The apparatus of claim 1, wherein each of the protrusions extends between 4 and 10 mm from the distal end of the respective anchor launcher.

3. The apparatus of claim 1, wherein each of the protrusions has a diameter between 0.05 and 0.3 mm.

4. The apparatus of claim 1, wherein in the relaxed state, each of the protrusions bends away from a centroid of the at least four anchor launchers.

5. The apparatus of claim 1, wherein each of the anchor launchers comprises a metal housing that is visualizable using fluoroscopy.

6. The apparatus of claim 1, wherein each of the protrusions is arranged so that when a protrusion in the deflected state is moved to a position at which the protrusion is no longer being pressed against the annulus or the tissue adjacent to the annulus, the protrusion returns towards the relaxed state.

7. The apparatus of claim 1, wherein each of the at least four anchor launchers comprises:

a housing shaped and dimensioned to accommodate a respective one of the at least four anchors, the housing having a distal end;

a spring that is movable between a compressed state and an expanded state, arranged with respect to the housing and the respective anchor so that movement of the spring from the compressed state to the expanded state drives the respective anchor out of the distal end of the housing; and an actuator configured to trigger movement of the spring from the compressed state to the expanded state upon actuation of the actuator.

8. The apparatus of claim 1, wherein each of the protrusions is affixed to a respective anchor launcher by at least one weld.

9. The apparatus of claim 1, wherein each of the protrusions is affixed to a respective pull wire that is used to trigger a respective anchor launcher.

10. The apparatus of claim 1, wherein the distal loop portion of the cord comprises an open loop having first and second ends, and wherein the cord has first and second proximal portions connected, respectively, to the first and second ends of the distal loop portion.

11. The apparatus of claim 1, wherein the distal loop portion of the cord is a closed loop.

12. A method for affixing a cord to an annulus, the method comprising:

positioning, in a vicinity of the annulus, (a) a cord having a distal loop portion, (b) at least four anchors distributed about the cord, wherein each of the at least four anchors is configured to anchor a respective region of the cord to the annulus or to tissue adjacent to the annulus, (c) at least four anchor launchers, each of the anchor launchers having a distal end, wherein each of the anchor launchers is configured to launch a respective one of the at least four anchors out of the anchor launcher's distal end so that the respective anchor becomes embedded in the annulus or the tissue adjacent to the annulus, and (d) at least four flexible radio-opaque protrusions, wherein each of the protrusions is arranged with respect to a respective one of the at least four anchor launchers so that the protrusion is free to move from a relaxed state to a deflected state, wherein in the relaxed state the protrusion protrudes distally beyond the distal end of the respective anchor launcher, wherein in the relaxed state, each of the protrusions is bent at an angle between 5° and 20° with respect to a longitudinal axis of the respective anchor launcher, and wherein each of the protrusions is shaped and arranged so that progressive advancement of the respective anchor launcher in a distal direction beyond a point at which the protrusion makes contact with the annulus or the tissue adjacent to the annulus results in progressive deflection of the protrusion;

adjusting a position of the anchor launchers until fluoroscopic images of the protrusions indicate that each of the protrusions is deflected beyond a threshold angle; and triggering each of the anchor launchers to launch a respective anchor at a time when fluoroscopic images of the protrusions indicate that each of the protrusions is deflected beyond the threshold angle.

13. The method of claim 12, wherein each of the protrusions extends between 4 and 10 mm from the distal end of the respective anchor launcher.

14. The method of claim 12, wherein each of the protrusions has a diameter between 0.05 and 0.3 mm.

15. The method of claim 12, wherein each of the protrusions is arranged so that when a protrusion in the deflected state is moved to a position at which the protrusion is no longer being pressed against the annulus or the tissue adjacent to the annulus, the protrusion returns towards the relaxed state.

16. A method for aligning a device with a target location, the method comprising:

arranging at least three flexible radio-opaque protrusions with respect to the device so that each of the protrusions is free to move from a relaxed state to a deflected state, wherein in the relaxed state the protrusion protrudes distally beyond the device, and wherein in the relaxed state, each of the protrusions is bent at an angle between 5° and 20° with respect to a longitudinal axis of the device, and wherein each of the protrusions is shaped and arranged so that progressive advancement of the device in a distal direction beyond a point at which the protrusion makes contact with a structure in the target location results in progressive deflection of the protrusion, and wherein each of the protrusions is arranged so that when a protrusion in the deflected state is moved to a position at which the protrusion is no longer being pressed against the structure, the protrusion returns towards the relaxed state;

positioning the device in a vicinity of the target location;

adjusting a position of the device until fluoroscopic images of the protrusions indicate that each of the protrusions is deflected beyond a threshold angle; and releasing the device at a time when fluoroscopic images of the protrusions indicate that each of the protrusions is deflected beyond the threshold angle.

17. The method of claim 16, further comprising anchoring the device in place at the time when fluoroscopic images of the protrusions indicate that each of the protrusions is deflected beyond the threshold angle.

18. The method of claim 16, wherein each of the protrusions extends distally beyond the device by between 4 and 10 mm.

19. The method of claim 16, wherein each of the protrusions has a diameter between 0.05 and 0.3 mm.

\* \* \* \* \*